(12) United States Patent
Braun et al.

(10) Patent No.: US 12,136,361 B2
(45) Date of Patent: Nov. 5, 2024

(54) ELECTRONIC LABELING ARRANGEMENT, METHOD FOR MANUFACTURING AN ELECTRONIC LABELING ARRANGEMENT, AND MEDICATION PACKAGE

(71) Applicant: Schreiner Group GmbH & Co. KG, Oberschleissheim (DE)

(72) Inventors: Uwe Braun, Munich (DE); Philipp Guggenmos, Neusaess (DE)

(73) Assignee: Schreiner Group GmbH & Co. KG, Oberschleissheim (DE)

( * ) Notice: Subject to any disclaimer, the term of this patent is extended or adjusted under 35 U.S.C. 154(b) by 335 days.

(21) Appl. No.: 17/770,779

(22) PCT Filed: Oct. 15, 2020

(86) PCT No.: PCT/EP2020/079019
§ 371 (c)(1),
(2) Date: Apr. 21, 2022

(87) PCT Pub. No.: WO2021/078622
PCT Pub. Date: Apr. 29, 2021

(65) Prior Publication Data
US 2022/0366815 A1      Nov. 17, 2022

(30) Foreign Application Priority Data
Oct. 22, 2019   (DE) .................... 10 2019 128 518.6

(51) Int. Cl.
*G09F 3/20* (2006.01)
*A61J 1/03* (2023.01)
*G09F 3/02* (2006.01)

(52) U.S. Cl.
CPC .............. *G09F 3/208* (2013.01); *A61J 1/035* (2013.01); *G09F 3/02* (2013.01); *A61J 2205/60* (2013.01)

(58) Field of Classification Search
CPC .... G09F 3/208; G09F 3/20; G09F 3/02; A61J 1/035; A61J 1/03; A61J 2205/60; G16H 40/20
(Continued)

(56) References Cited

U.S. PATENT DOCUMENTS 6,244,452 B1    6/2001  Morano et al.
7,113,101 B2    9/2006  Petersen et al.
(Continued)

FOREIGN PATENT DOCUMENTS

DE    10 2004 060 213 A1    7/2005
EP     1 737 750 B1        10/2007
(Continued)

OTHER PUBLICATIONS

International Search Report in PCT/EP2020/079019, mailed Feb. 1, 2021.
(Continued)

*Primary Examiner* — Justin V Lewis
(74) *Attorney, Agent, or Firm* — Collard & Roe, P.C.

(57) ABSTRACT

An electronic labeling arrangement for attachment to a medication package includes a protective member, having a covering portion and cavities, and a predetermined formed protrusion; a conductor track film having conductor tracks and cavities, at least one conductor track being associated with each respective track film cavity so that the conductor track crosses the respective track film cavity at least in sections; and an electronic unit coupled to the conductor tracks and arranged to detect a change in resistance of a respective conductor track. The protective member and the conductor track film are coupled such that the covering portion covers a track film top side, and the protective member cavities and the track film cavities are arranged one above the other and overlap at least in sections. The pro-
(Continued)

trusion covers an underside of the conductor track film, so that the covering portion and the protrusion surround the electronic unit.

16 Claims, 5 Drawing Sheets

(58) Field of Classification Search
USPC ............. 40/124.06; 206/581, 823; 281/51; 283/72, 74, 79, 81, 83, 94, 98, 117
See application file for complete search history.

(56) References Cited

U.S. PATENT DOCUMENTS

| | | | |
|---|---|---|---|
| 8,151,990 | B2 | 4/2012 | Udo et al. |
| 2014/0048442 | A1 | 2/2014 | Maijala et al. |
| 2015/0290085 | A1* | 10/2015 | Niven ................ A61J 7/04 222/23 |
| 2017/0330845 | A1 | 11/2017 | Mijala |

FOREIGN PATENT DOCUMENTS

| | | |
|---|---|---|
| EP | 3 025 697 A1 | 6/2016 |
| JP | 2013-31638 A | 2/2013 |
| NL | 2006666 C2 | 10/2012 |
| WO | 2009/135283 A1 | 11/2009 |
| WO | 2012/055021 A1 | 5/2012 |
| WO | 2014/044918 A1 | 3/2014 |
| WO | 2014/076501 A1 | 5/2014 |
| WO | 2015/183203 A1 | 12/2015 |

OTHER PUBLICATIONS

German Search Report in DE 10 2019 128 518.6, dated Jul. 6, 2020, with English translation of relevant parts.

* cited by examiner

ELECTRONIC LABELING ARRANGEMENT, METHOD FOR MANUFACTURING AN ELECTRONIC LABELING ARRANGEMENT, AND MEDICATION PACKAGE

CROSS REFERENCE TO RELATED APPLICATIONS

This application is the National Stage of PCT/EP2020/079019 filed on Oct. 15, 2020, which claims priority under 35 U.S.C. § 119 of German Application No. 10 2019 128 518.6 filed on Oct. 22, 2019, the disclosure of which is incorporated by reference. The international application under PCT article 21 (2) was not published in English.

The present invention relates to an electronic labeling arrangement and a method for manufacturing an electronic labeling arrangement, which provide a reliable, electronically detectable medication withdrawal in a simple and cost-effective manner. The invention further relates to a medication package having such an electronic labeling arrangement.

Labels can be used for authorization or proof of origin and can be used wherever it is necessary to identify or verify items. For example, labels are used to mark medication packaging to provide required information. In the field of medication of persons, it is useful to monitor a medication intake in a controlled manner, for example, in order to comply with a predetermined medication schedule.

It is a challenge underlying the invention to provide an electronic labeling arrangement and a method for manufacturing an electronic labeling arrangement, each of which enables a reliably detectable medication withdrawal in a simple and cost-effective manner.

The challenge is solved by the features of the independent patent claims. Advantageous further embodiments are indicated in the respective subclaims.

According to one aspect of the invention, an electronic labeling arrangement for attachment to a medication package comprises a protective member having a covering portion with a plurality of cavities formed spaced apart from each other and having a predetermined protrusion formed adjacent to the covering portion, wherein a fold line is provided between the covering portion and the protrusion. The labeling arrangement further has a conductor track film comprising a plurality of conductor tracks and a plurality of cavities. The conductor tracks are respectively formed spaced apart from each other, and the cavities of the conductor track film are respectively formed spaced apart from each other. At least one conductor track is associated with a respective cavity of the conductor track film, such that the conductor track crosses the respective cavity of the conductor track film at least in sections. Furthermore, the labeling arrangement has an electronic unit which is coupled to the conductor tracks and is configured to detect a change in resistance of a respective conductor track. Further, the protective member and the conductor track film are coupled to each other such that the covering portion covers an upper surface of the conductor track film so that the cavities of the protective member and the cavities of the conductor track film are arranged one above the other and overlap at least in sections. Further, the protective member and the conductor track film are coupled to each other such that the protrusion covers an underside of the conductor track film so that the electronic unit is surrounded by the covering portion and the protrusion of the protective member.

By means of the described electronic labeling arrangement, a reliably detectable medication withdrawal can be realized in a simple and cost-effective manner. In particular, the labeling arrangement makes it possible to retrofit medication blisters or so-called multi-dose cards, which comprise a plurality of usually tablet-shaped medications. In this way, the labeling arrangement can be used to set up electronic monitoring of a drug withdrawal. The electronic labeling arrangement may also be referred to as an intelligent card layer or smart layer card.

It is a finding in connection with the present invention that there are a variety of medication blisters and multi-dose cards that have different designs and different shapes. The described labeling arrangement enables to easily and inexpensively equip such medication packages with electronics and can be attached thereto with little effort.

The labeling arrangement has, for example, an adhesive layer which is attached to the underside of the conductor track film and which enables simple and reliable attachment of the labeling arrangement to a medication blister. In this case, the labeling arrangement is designed in particular to match the medicament blister, so that the labeling arrangement can be bonded to the medicament blister in such a way that the cavities of the labeling arrangement overlap with the cavities of the medicament blister and can be arranged, for example, congruently one above the other.

As soon as a tablet is pressed out of a cavity of the medication blister, the tablet also passes through the cavities of the conductor track film and causes destruction or breakage of the associated conductor track film, which can be detected as a change in resistance or also as a change in conductivity of the conductor track film by means of the electronic unit. In the case of such an event, for example, a time information in the form of a time stamp and a position information are then stored in the electronic unit, which provides information about through which cavity of the conductive track foil the tablet was removed.

The electronic unit is designed, for example, as a PCB (printed circuit board) with an integrated RFID unit, in particular an NFC unit, and is in signal contact with the conductor tracks of the conductor track film. Alternatively or additionally, the electronic unit can be set up to enable signal technology communication by means of Bluetooth or GSM as data transmission technology.

The electronic unit is designed in particular as a circuit board equipped with electronic components. This includes, among other things, a chip or micro-controller. For example, the electronic unit further has resistors, a battery, a quartz clock and/or an antenna structure and forms a so-called integrated circuit board. In particular, the electronic unit may be partially manufactured by printing.

The electronic unit is configured to detect an interruption or change in the conductive tracks and to store it as an event. The stored events can then be queried by means of a reader, such as an RFID reader or a smartphone, which has the appropriate reading capability. Thus, it is possible to check whether a predetermined medication schedule has been adhered to.

According to a preferred further embodiment, the protective member can be inexpensively and stably made of cardboard or have a cardboard element. Alternatively or additionally, the protective member is made of foil or has a foil element. The protective member forms a stable and protective support for the conductor track film and in particular for the electronic unit.

According to a further embodiment of the electronic labeling arrangement, the electronic unit is designed to be replaceable and the protective member has a recess in the area of the electronic unit. The electronic unit can be inserted through the recess in the protective member and coupled to the conductor tracks of the conductor track foil. Correspondingly, the electronic unit can also be removed through the recess of the protective element and decoupled from the conductor tracks of the conductor track film.

In this way, the electronic unit can be replaced or continued to be used after, for example, a patient-specific drug blister or drug blister has been emptied. The recess in the protective member forms an opening or window in which the conductor tracks of the conductive track film converge.

The electronic unit may be bonded to the conductor track film and/or the protective member in the area of the recess. In particular, the electronic unit can be integrally formed or arranged in or on the protective element or the conductor track film. Alternatively or additionally, the electronic unit is connected to the conductive track film and/or the protective member in a manner such that it can be plugged on or pressed on, thus enabling easy replacement.

According to a further embodiment of the labeling arrangement, the conductor tracks are applied to the upper side of the conductor track film by means of printing or etching, the upper side facing the covering section of the protective member.

According to a further embodiment of the labeling arrangement, the conductor track film has an adhesive layer arranged on the underside, the underside facing away from the covering section of the protective member. This enables easy and reliable attachment of the labeling arrangement to a drug package. For example, the adhesive layer can be printed on the underside and cover the spaces between the cavities. For later use, the adhesive layer is preferably covered with an easily separable or easily removable siliconized film or silicone paper.

According to a further embodiment of the labeling arrangement, the protective member has an adhesive layer that adhesively bonds the protective member to the conductor track film. The adhesive layer is then provided, for example, like the previously described adhesive layer of the conductive track foil, between the cavities of the protective member and allows simple and reliable attachment of the protective member to the upper surface of the conductive track film. In addition, the adhesive layer can also extend into the area of the protrusion of the protective member, so that this can be bonded to the underside of the conductive track film after folding over along the fold line and protectively encloses or embeds the electronic unit. Alternatively or additionally, the overhang can also be connected to the underside of the conductor track film by means of hooking, by means of Velcro and/or by means of heat sealing.

The embedding of the electronic unit can thus be irreversibly designed, so that decoupling of the folded-over protrusion from the underside of the conductor track film cannot be carried out non-destructively. However, the embedding of the electronic unit can also be reversible by means of hooking label sections or by means of Velcro elements, so that decoupling of the folded-over projection from the underside of the conductor track film can take place non-destructively.

According to a preferred further embodiment of the labeling arrangement, the electronic unit comprises an RFID transponder and/or a printed circuit board. In particular, the electronic unit may be designed as a partially printed circuit or as a so-called printed circuit board.

Furthermore, the labeling arrangement may be further configured such that the printed circuit board comprises perforations, each of which delimits a cavity of the printed circuit board. In this way, for example, a tablet can be easily pushed out of a tablet blister and released through the cavities of the conductive track foil and the protective member arranged thereabove. Accordingly, the conductive track film is preferably provided with a special perforation in the region of the cavities, which allows a medication to be easily pressed out of or removed from the cavity.

The protective member is preferably in the form of printed and die-cut cardboard and is bonded to the conductive track film. The cardboard is punched out in the area of the cavities. Thus, the cavities of the cardboard form free recesses or openings, while the cavities of the conductor track film are covered by foil elements which are broken open when a respective tablet is pressed through. The electronic unit connected to the conductor track label is integrated in the carton, for example, on a rear side or underside facing the conductor track label. In the area of the electronic unit, the carton has the overhang, in particular in the form of an overhanging carton area, which is folded back over or around the electronic unit and glued. This means that the electronic unit is no longer visible and is stably and securely integrated into two cardboard layers of the protective member. In addition, the cardboard box or the protective member may have one or more tabs that form the function of a positioning aid when attaching the labeling arrangement to a medication package.

In particular, the smart cardboard or smart labeling arrangement can be adapted to existing multi-dose cards and allows the multi-dose cards to remain unchanged and to be printed in advance with individual patient/medication data and filled with pills or medications according to the specifications. The electronic labeling arrangement is then placed as the top layer on the multi-dose card and fixed in place, for example, using a coated adhesive. Since the conductor label preferably consists of or has a transparent film element, such as a PET film, it allows reading of the text information printed on the underlying layer, which is deposited on a paper layer, for example.

The electronic labeling arrangement described thus provides a sensor technology that can be used to monitor each individual removal of a tablet from a single cavity. During a medication withdrawal, in particular, data such as a time stamp and a cavity affiliation can be automatically stored in the electronic unit and read out using transmission technologies such as RFID, Bluetooth or GSM. The electronic unit can also be designed as a reusable labeling component.

By means of the electronic labeling arrangement, an adaptable or integrable solution for existing multi-dose cards can thus be realized. This also makes it possible, for example, to print on the protective member before it is coupled to the electronic unit. In comparison, with an individual solution, no printing is possible in advance, since a cardboard box equipped with electronics cannot be fed through a printer. In addition, the described labeling arrangement contributes to an unchanged use of a multi-dose card by patients, since no change is required with respect to usual processes, for example in a pharmacy, which include a filling, an assembly of the tablet blister and the multi-dose card. Familiar processes, such as a simple push-through with the multi-dose card or tablet blister virtually unchanged, are also maintained in a patient.

In accordance with a further aspect of the invention, an electronic medication package includes a container for medications, and an embodiment of the previously described electronic labeling arrangement coupled to the container. For example, the medication package is formed as a tablet blister or multi-dose card having a plurality of cavities, wherein the electronic labeling arrangement is arranged on the tablet blister such that the cavities of the protective member and the cavities of the conductor track film are arranged over the cavities of the tablet blister and overlap at least in sections. Alternatively, the medicament package is formed, for example, as a foldable medicament sleeve, wherein the electronic labeling arrangement is arranged on an outer side of the medicament sleeve.

The foldable medicament sleeve comprises, for example, a cardboard cover surrounding a tablet blister. The tablet blister typically has a plastic film or plastic tray with cavities for receiving tablets covered with an aluminum foil.

The cover thus forms a foldable cardboard sleeve coupled to the tablet blister.

The labeling arrangement is thus suitable as a smart layer card not only for use directly on tablet blisters, but can also be adhered to foldable medication wrappers to provide electronic detection of a medication withdrawal. In that the medication package comprises an embodiment of the described electronic labeling arrangement, described properties and features of the labeling arrangement are also disclosed for the medication package, and vice versa.

According to a further aspect of the invention, a method for manufacturing an electronic labeling assembly for attachment to a medication package comprises providing a protective member having a covering portion with a plurality of cavities formed spaced apart from each other and having a predetermined protrusion formed adjacent the covering portion, wherein a fold line is provided between the covering portion and the protrusion. The method further comprises providing a conductor track foil having a plurality of conductor tracks and a plurality of cavities, each of which is formed spaced apart from each other, wherein a respective cavity of the conductor track foil is associated with a respective conductor track and the conductor track crosses the respective cavity of the conductor track foil at least in sections. The method further comprises providing an electronic unit and coupling the electronic unit to the conductor tracks of the conductor track foil, so that a change in resistance of a respective conductor track can be detected by means of the electronic unit. The method further comprises coupling the protective member with the conductor track foil in such a way that the covering section covers an upper side of the conductor track foil, so that the cavities of the protective member and the cavities of the conductor track foil are arranged one above the other and overlap at least in sections. The method further comprises folding the overhang along the fold line so that the overhang covers an underside of the conductor track film and thereby embedding the electronic unit between the covering portion and the overhang of the protective member.

Providing the protective member may include, for example, providing a cardboard and/or foil member from which segments are punched out of the covering portion, thereby forming the plurality of cavities of the protective member. Providing the conductor track film may comprise providing a foil element on which the conductor tracks and/or the electronic unit are printed or applied.

In particular, the method is arranged for producing an embodiment of the electronic labeling arrangement described above. Therefore, described properties and features of the labeling arrangement are also disclosed for the method for manufacturing an electronic labeling arrangement, and vice versa.

The method may further be extended to attach the manufactured electronic labeling arrangement to a tablet blister, a multi-dose card, or a foldable medication sleeve.

In the following, embodiments of the invention are explained with reference to schematic drawings. They show.

Elements or features of the same design or function are identified with the same reference signs throughout the figures. For reasons of clarity, not all of the elements or features shown in all of the figures are identified with the corresponding reference signs, possibly.

Figure 1:
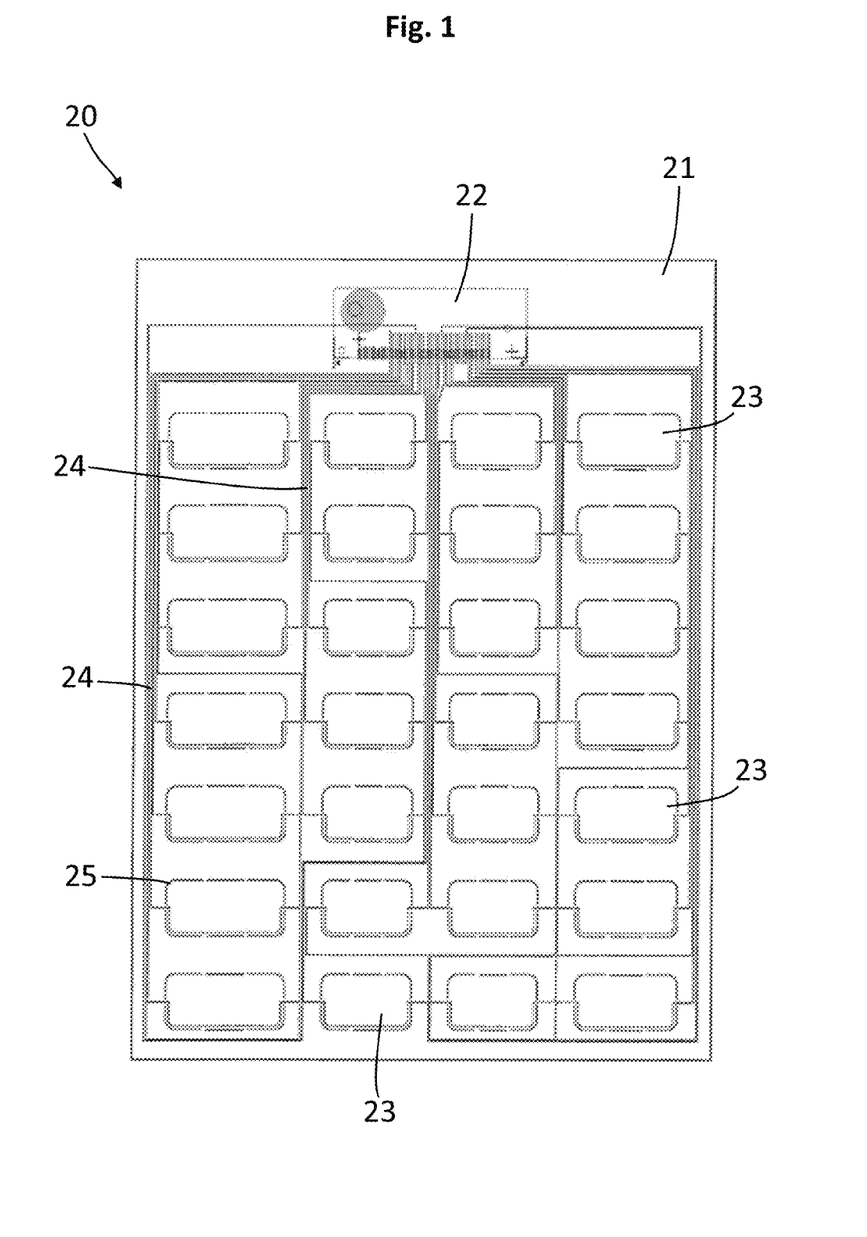
FIG. 1 an embodiment of a conductor track film with an electronic unit for an electronic labeling arrangement, FIG. 2 an embodiment of a protective member for the electronic labeling arrangement, FIGS. 3-4 embodiments of a cross-section of the electronic labeling arrangement, FIG. 5 a further embodiment of a cross-section of the conductor track film for the electronic labeling arrangement, FIG. 6 a further embodiment of the electronic labeling arrangement, and FIG. 7 a flow chart for a method of manufacturing the electronic labeling arrangement according to FIGS. 1-6.
Figure 5:
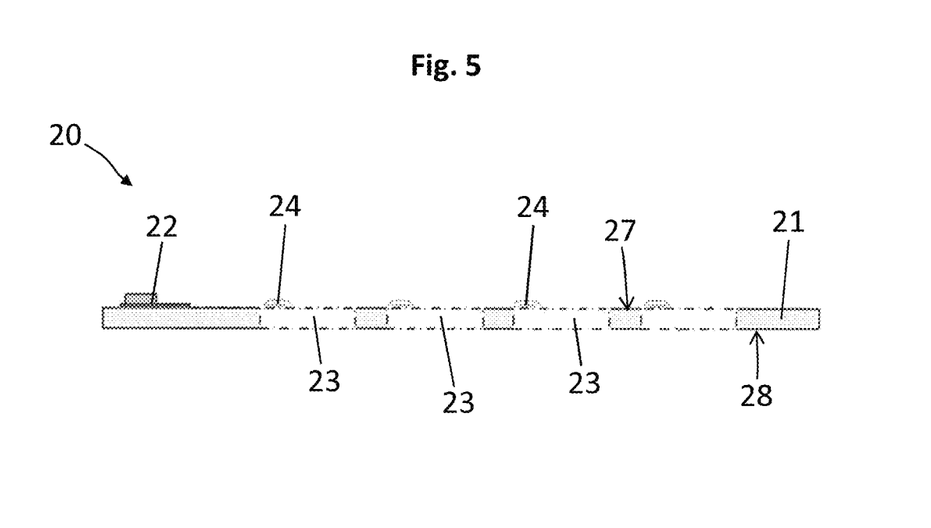

FIG. 1 shows a schematic top view of a conductor track film 20 for an electronic labeling arrangement 1 for attachment to a medication package, such as a tablet blister or a foldable medicament sleeve. A schematic side view of the conductive track foil 20 is shown in FIG. 5. The conductor track film 20 has a foil element 21 on which a plurality of conductor tracks 24 are formed spaced apart from each other, for example by means of etching or printing. In addition, the foil element 21 has a plurality of cavities 23 formed spaced apart from each other. The cavities are also each bounded by a predetermined perforation 25, which allow a tablet or drug to be easily pushed through a respective cavity 23 of the foil element 21.

At least one conductor track 24 is associated with a respective cavity 23, which crosses the cavity 23 at least in sections. The conductor tracks 24 converge in an upper region or a head region of the conductor track film 20 and are coupled to an electronic unit 22. The electronic unit 22 is designed as a so-called printed circuit board with an integrated RFID unit and is set up to detect a change in resistance or conductivity of a conductor track 24 and to assign such an event to the corresponding cavity 23.

Figure 2:
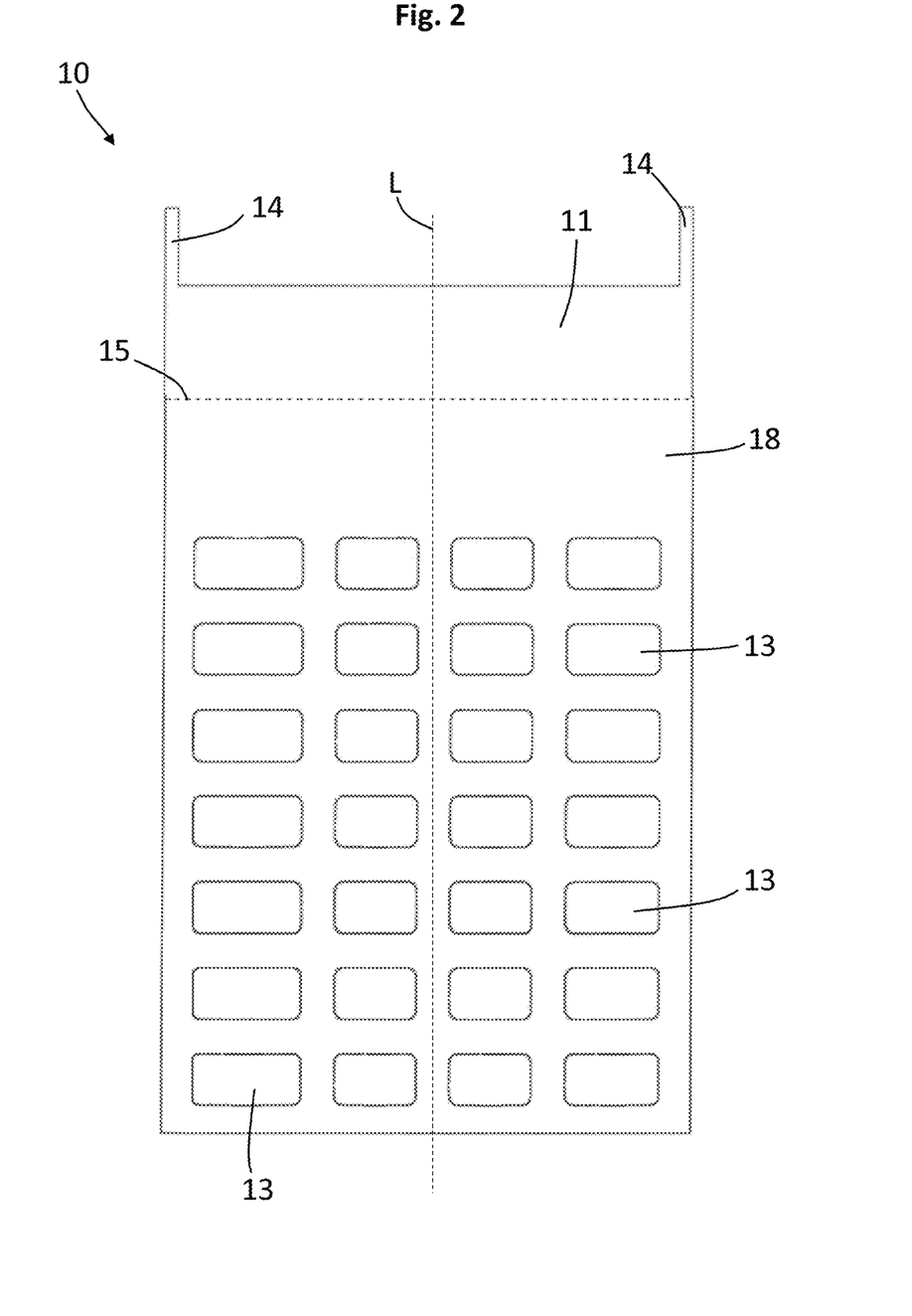

FIG. 2 shows a schematic top view of a protective member 10 for the electronic labeling arrangement 1. The protective member 10 is made, for example, of cardboard and has a plurality of cavities 13 which are formed at a distance from one another. The cavities 13 are realized as openings or recesses and are formed, for example, by means of punching and in particular in shape and position in coordination with the cavities 23 of the foil element 21.

The cavities 13 are formed in a covering portion 18 of the protective member 10, which adjoins a protrusion 11 of the protective member 10. A fold line 15 is introduced between the protrusion 11 and the covering portion 18, which allows controlled folding and folding of the protrusion 11 relative to the covering portion 18. With respect to a longitudinal axis L of the protective member 10, the protrusion 11 is formed in a head portion of the protective member 10 and serves to safely and reliably protect the electronic unit 22, as will be explained below.

Furthermore, as illustrated in FIG. 2, the protective member 10 may comprise positioning elements 14 in the form of protruding ribbon-shaped sections extending from the projection 11. Such positioning elements 14 enable a particularly simple and precise attachment of the labeling arrangement 1 to a medicament package, such as a tablet blister. A distance between the positioning elements 14 is preferably matched to a width of the tablet blister to be attached, so that the cavities of the tablet blister and the cavities 13 and 23 of the protective member 10 and the conductor track film 20 are aligned with each other and substantially superimposed. The positioning elements 14 and an intervening edge of the protrusion 11 thus provide an outer edge for the tablet blister to contact in a folded down state.

Figure 3:
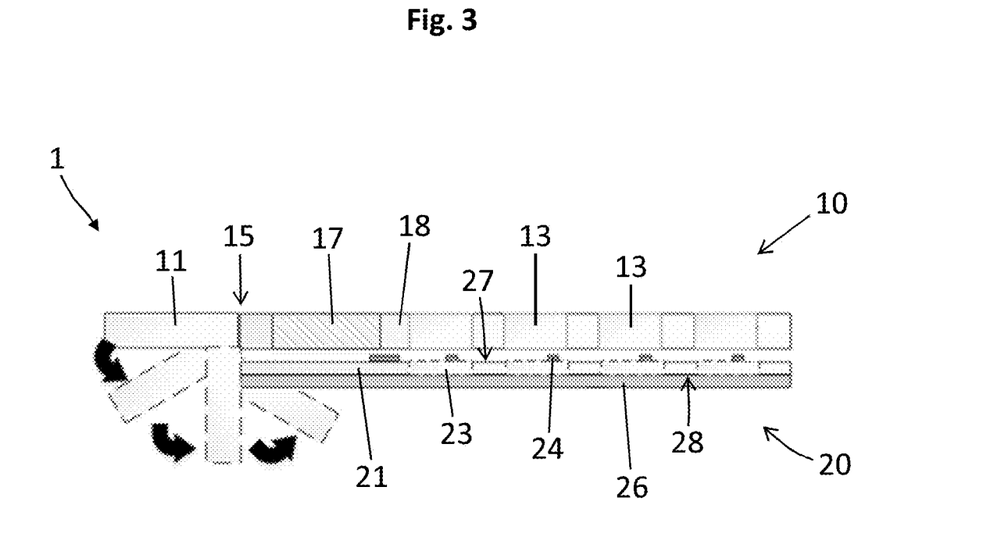
Figure 4:
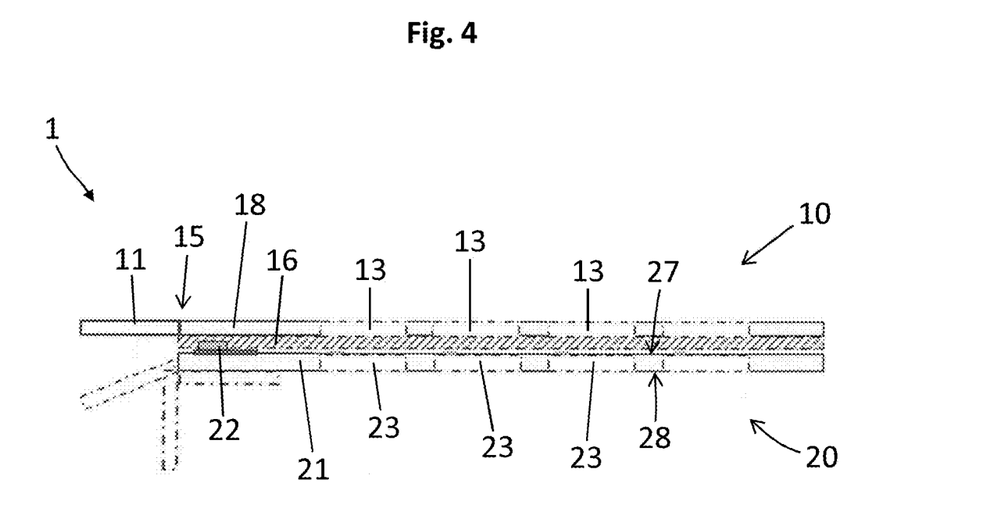

FIGS. 3 and 4 show, in a respective schematic side view, embodiments of the electronic labeling arrangement 1 with the protective member 10 and the conductor track film 20. In each case, it is indicated that the projection 11 of the protective member 10 protrudes beyond the conductor track film 20, so that the protrusion 11 can be selectively folded over along the fold line 15 and coupled to an underside 28 of the foil element 21. The covering portion 18 is associated with an upper side 27 of the foil element 21 and, with respect to its cavities 13, is formed in such a way that these overlap, at least in sections, with the cavities 23 of the conductor track film 20. Preferably, the cavities 13 and 23 of the protective member 10 and of the conductor track film 20 are formed and arranged in such a way that they lie substantially congruently one above the other.

The protrusion 11 has a predetermined length, so that the electronic unit 22 is enclosed by the protective member 10 on an upper side and a lower side. Thus, after the protrusion 11 has been folded down, the electronic unit 22 is securely and reliably embedded, surrounded or enclosed in the protective member 10 and protected from external influences.

FIG. 3 further illustrates that the protective member 10 may include a recess 17 through which the electronic unit 22 may be inserted and removed. Thus, the electronic unit 22 may be formed as a replaceable component of the electronic labeling arrangement 1 and may be coupled to the conductor track film 20 and the conductor tracks 24 formed thereon, for example, by means of insertion or pressing. Alternatively, the electronic unit 22 is, for example, bonded to the conductive track film 20 and/or the protective member 10 and cannot be non-destructively removed.

The conductor tracks 24 are formed on the upper side 27 of the foil element 21 and cross a respective cavity 23 through which a tablet can be removed (see FIG. 3). During such an operation, the perforated foil section of the foil element 21 covering the associated cavity 23 is broken and lifted, causing an interruption or change in the electrical resistance of the conductor track 24 above it. The electronic unit 22 can detect such a change in resistance and store it as a removal event with an associated time stamp. A readout of the electronic unit 22 thus enables electronic, automated monitoring of a medication plan and contributes to a safe and reliable treatment plan for a patient, in that the electronic labeling arrangement 1 is applied to a provided multi-dose blister, for example.

FIG. 3 further illustrates that the conductor track film 20 has an adhesive layer 26 attached, for example printed, to the underside 28 of the foil element 21. The adhesive layer 26 enables easy and reliable attachment of the labeling arrangement 1 to a medication package, such as the multi-dose blister. Referring to FIG. 1, the conductor track film 20 may be covered with the adhesive layer 26 on the underside 28 except for the regions of the cavities 23 or completely. The adhesive layer 26 may further be used to secure the folded over protrusion 11 of the protective member 10 to the underside 28 of the conductor track film 20.

Referring to FIG. 4, the protective member 10 may also have an adhesive layer 16 on its underside facing the conductor track film 20. Referring to FIG. 2, the protective member 10 may be covered with the adhesive layer 16 on its underside except for the regions of the cavities 13 or completely. In this way, the protective member 10 can be easily and reliably adhesively bonded to the conductor track film 20. In addition, the conductor tracks 24 and the electronic unit 22 can thus be embedded and protected in the adhesive layer 16.

Alternatively, or in addition to the adhesive layer 16, an adhesive layer may be provided on the upper surface 27 of the foil element 21, covering the upper surface 27 completely or partially except for the regions of the cavities 23.

The adhesive layer 16 may also extend into the area of the protrusion 11 on the underside of the protective member 10, and may be used to secure the folded-over protrusion 11 of the protective member 10 to the underside 28 of the conductor track film 20. Alternatively or additionally, the protrusion 11 can be coupled to the underside 28 of the foil element 21 by means of a Velcro fastening element, by means of heat sealing or by means of hooking and protectively enclose the electronic unit 22.

Figure 6:
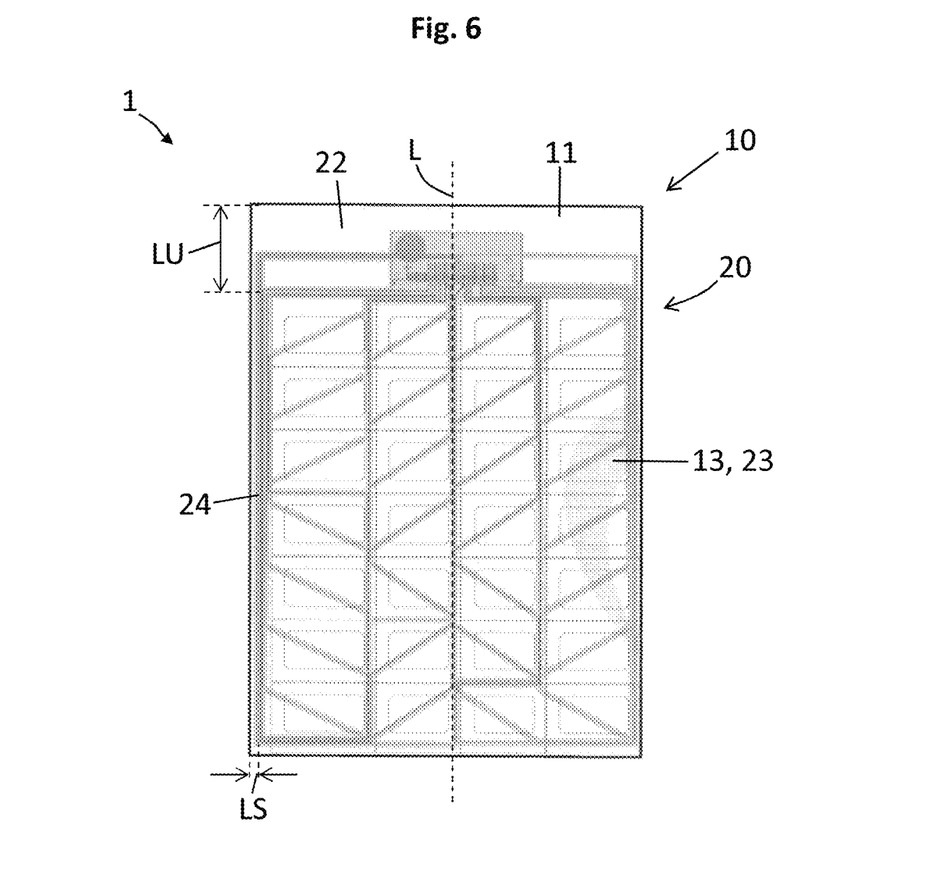

FIG. 6 shows in a schematic top view a further embodiment of the electronic labeling arrangement 1, in which a respective conductor track 24 diagonally crosses an associated cavity 23.

Furthermore, it is illustrated that the protrusion 11 protrudes over the conductor track film 20 in a predetermined manner with respect to the longitudinal axis L, so that it forms a length LU in this respect when folded over. Also, a lateral projection of the protective member 10 over the conductive track film 20 and/or a medication package may be predeterminedly formed to form a stable and secure cover. Illustrated is a lateral projection having a length LS.

By means of the described electronic labeling arrangement 1, a reliably detectable medicament removal can be realized in a simple and inexpensive manner. In particular, the labeling arrangement 1 makes it possible to retrofit medication blisters or so-called multi-dosage cards, which comprise a plurality of usually tablet-shaped medications. In this way, by means of the labeling arrangement 1, a convenient electronic monitoring of a medication withdrawal can be set up, which automatically detects withdrawal events and provides and stores them with associated information, such as time of withdrawal and position or number of the associated cavity.

Figure 7:
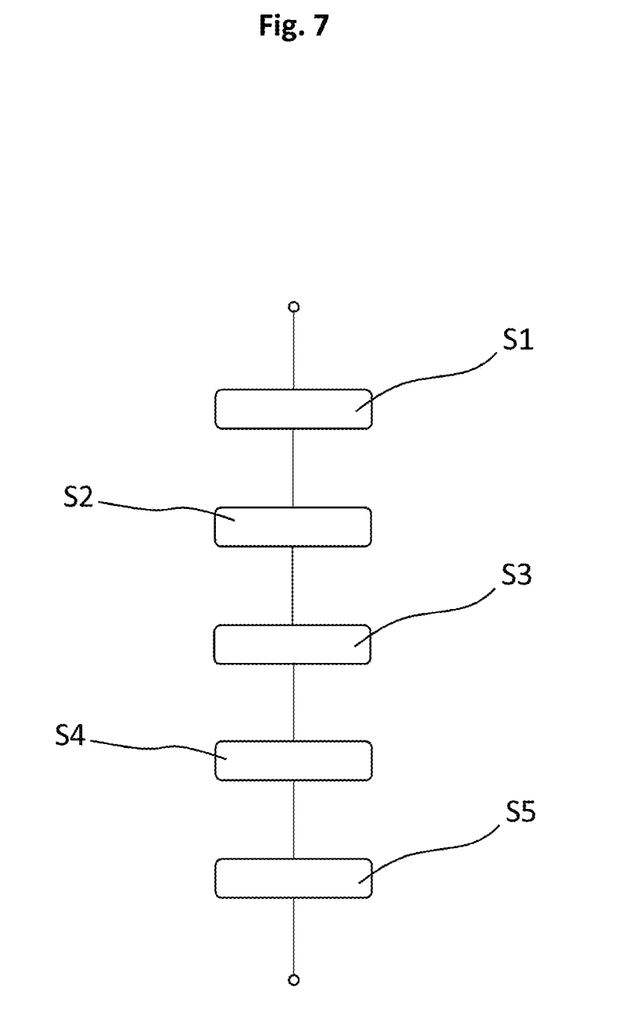

A method for manufacturing an embodiment of the electronic labeling arrangement 1 may be carried out according to the flow chart as shown in FIG. 7. In a step S1, the protective member 10 is provided. The providing may comprise punching out the cavities 13 and inserting the fold line 15 and thus forming the covering portion 18 and the protrusion 11.

In a further step S2 of the method, the conductor track film 20 is provided with a plurality of conductor tracks 24 and a plurality of cavities 23. The providing may include inserting the perforations 25 delimiting the respective cavities 23. Further, providing may include printing or etching the conductor tracks 24 on the upper surface 27 of the foil element 21.

In a further step S3 of the method, the electronic unit 22 is provided and coupled to the conductor tracks 24 of the conductor track film 20. The providing may thereby comprise a partial imprinting of elements of the electronic unit 22. Alternatively, the providing may comprise a plugging or pressing of the electronic unit 22 onto the conductor track film 20, for example through a recess 17 of the protective member 10 provided for this purpose.

In a step S4, coupling of the protective member 10 to the conductor track film 20 is carried out, for example by means of bonding with the adhesive layer 16 to the upper side 27 of the foil element 21. The coupling is carried out in such a way that the covering portion 18 covers the upper side 27 of the conductor track film 20 or of the foil element 21, so that the cavities 13 of the protective member 10 and the cavities 23 of the conductor track foil 20 are arranged one above the other and overlap at least in sections.

In a step S5, the protrusion 11 is folded over along the fold line 15 so that the protrusion 11 covers the underside 28 of the foil element 21 and thereby the electronic unit 22 is embedded between the covering section 18 and the protrusion 11 of the protective element 10.

By means of the described method, an embodiment of the electronic labeling arrangement 1 can be realized, which enables a beneficial and convenient extension of a medication packaging. In particular, the labeling arrangement 1 is adaptable for multi-dose cards or multi-tablet blisters and can be manufactured simply and inexpensively. The multi-dose card already provides barrier layers in the form of aluminum and/or paper layers, which form a secure separation of the medications located in the cavities from the labeling arrangement 1. Thus, when the electronic labeling arrangement 1 is attached to the medication package, there is no direct contact with the drugs. Handling and printing of the multi-dose cards can be carried out as before.

The electronic labeling arrangement 1 implements a type of intelligent two-layer card overlay or smart layer card that can also be adhered to an outer surface of a commercially available medication package, such as a multi-dose card or tablet blister, to electronically detect a removal of individual tablets. The conductive tracks 24 are disposed over the cavities 23 of the conductor track film 20 and are interrupted or altered when a tablet is removed, which is detected by the electronic unit 22. The conductor track film 20 is bonded, for example, to the protective member 10 in the form of a cardboard package, the cardboard package being punched out in the region of the cavities 13 and having the protrusion 11 in the form of a projecting flap which is folded around the electronic unit 22 and thereby protects the latter from external influences. After a complete application of the labeling arrangement 1, the protective member 10 thus surrounds the electronic unit 22 in a sandwich-like manner. The electronic unit 22 is enclosed by the protrusion 11 and the covering portion 18, or is embedded between the protrusion 11 and the covering portion 18.

As an alternative to the cardboard of the two-layer labeling arrangement 1, a film may be used to stabilize and protect the conductor track film 20 and the electronic unit 22. In addition, the cardboard or film of the protective member 10 may include the recess 17 which allows the electronic unit 22 to be non-destructively detached from the remainder of the smart layer card for reuse.

LIST OF REFERENCE SIGNS 1 electronic labeling arrangement
10 stabilizing protective member
11 foldable protrusion
13 cavity of the protection member
14 positioning element
15 folding line
16 adhesive layer
17 recess
18 covering portion
20 conductor track film
21 foil element
22 electronic unit/RFID transponder
23 cavity of the conductor track film
24 conductor track
25 perforation
26 adhesive layer
27 top side of the conductor track film
28 underside of the conductor track film
L longitudinal axis of the labeling arrangement
LS lateral overlap
LU overlap of the folded-over protrusion
S(i) steps of a method for manufacturing an electronic labeling arrangement

The invention claimed is:

1. An electronic labeling arrangement for attachment to a medication package, comprising:
 a protective member having a covering portion with a plurality of cavities, each cavity of the plurality of cavities of the protective member formed spaced apart from each other cavity of the plurality of cavities of the protective member and the protective member further having a predetermined formed protrusion formed adjacent to the covering portion, wherein a fold line is provided between the covering portion and the protrusion,
 a conductor track film, which has a plurality of conductor tracks and a plurality of cavities, each cavity of the plurality of cavities of the conductor track film formed spaced apart from each other cavity of the plurality of cavities of the conductor track film, a respective cavity of the plurality of cavities of the conductor track film being assigned a respective conductor track of the plurality of conductor tracks and the respective conductor track crossing the respective cavity of the conductor track film at least in sections, and
 an electronic unit which is coupled to the plurality of conductive tracks and is configured to detect a change in resistance of a respective conductor track of the plurality of conductor tracks, the protective member and the conductor track film further being coupled to one another in such a way that the covering portion covers a top side of the conductor track film so that the plurality of cavities of the protective member and the plurality of cavities of the conductor track film are arranged one above the other and overlap at least in sections, and in that the protrusion covers an underside of the conductor track film, so that the electronic unit is surrounded by the covering portion and the protrusion of the protective member.

2. The electronic labeling arrangement according to claim 1, wherein the protective member is made of cardboard or comprises a cardboard element.

3. The electronic labeling arrangement according to claim 1, wherein the protective member is made of foil or comprises a foil element.

4. The electronic labeling arrangement according to claim 1, in which the plurality of conductor tracks is applied by means of printing or etching to the top side of the conductor track film, which faces the covering portion of the protective member.

5. The electronic labeling arrangement according to claim 1, in which the electronic unit is arranged integrated in the protective member or in the conductor track film.

6. The electronic labeling arrangement according to claim 1, in which the conductor track film has an adhesive layer arranged on the underside facing away from the covering portion of the protective member.

7. The electronic labeling arrangement according to claim 1, wherein the protective member comprises an adhesive layer adhesively bonding the protective member to the conductor track film.

8. The electronic labeling arrangement according to claim 1, wherein the electronic unit comprises an RFID transponder and/or a printed circuit board.

9. The electronic labeling arrangement according to claim 1, wherein the conductor track film comprises perforations each delimiting a respective cavity of the plurality of cavities of the conductor track film.

10. A medication package, comprising:
a container for medications, and
the electronic labeling arrangement according to claim 1, coupled to the container.

11. The medication package according to claim 10, formed as a foldable medication sleeve, wherein the electronic labeling arrangement is arranged on an outer side of the medication sleeve.

12. The medication package according to claim 10, which is formed as a tablet blister with a plurality of cavities, wherein the electronic labeling arrangement is arranged on the tablet blister such that the plurality of cavities of the protective member and the plurality of cavities of the conductor track film are arranged above the plurality of cavities of the tablet blister and overlap at least in sections.

13. The electronic labeling arrangement according to claim 1, in which the electronic unit is designed to be replaceable and the protective member has a recess in a region of the electronic unit, so that the electronic unit can be inserted through the recess of the protective member and coupled to the plurality of conductor tracks of the conductor track film and can be removed through the recess of the protective member and decoupled from the plurality of conductor tracks of the conductor track film.

14. A method of manufacturing an electronic label arrangement for attachment to a medication package, comprising:
providing a protective member having a covering portion with a plurality of cavities, each cavity of the plurality of cavities of the protective member formed spaced apart from each other cavity of the plurality of cavities of the protective member and the protective member having a predetermined formed protrusion formed adjacent to the covering portion, wherein a fold line is provided between the covering portion and the protrusion,
providing a conductor track film which has a plurality of conductor tracks and a plurality of cavities, each cavity of the plurality of cavities of the conductor track film formed spaced apart from each other cavity of the plurality of cavities of the conductor track film, a respective cavity of the plurality of cavities of the conductor track film being assigned to a respective conductor track of the plurality of conductor tracks and the respective conductor track crossing the respective cavity of the conductor track film at least in sections,
providing an electronic unit,
coupling the electronic unit to the plurality of conductor tracks of the conductor track film, so that a change in resistance of a respective conductor track of the plurality of conductor tracks can be detected by means of the electronic unit,
coupling the protective member to the conductor track film in such a way that the covering portion covers a top side of the conductor track film, so that the plurality of cavities of the protective member and the plurality of cavities of the conductor track film are arranged one above the other and overlap at least in sections, and
folding over the protrusion along the fold line so that the protrusion covers an underside of the conductor track film and thereby enables the electronic unit to be surrounded by the covering portion and the protrusion of the protective member.

15. The method according to claim 14, wherein providing the protective member comprises
cardboard and/or foil, and wherein the method further comprises the step of
punching segments from the covering portion and thereby forming the plurality of cavities of the protective member.

16. The method according to claim 14, wherein providing the conductor track film comprises:
providing a foil element, and
printing the plurality of conductor tracks and/or the electronic unit on the foil element.

* * * * *